(12) United States Patent
Paulos

(10) Patent No.: US 9,445,804 B2
(45) Date of Patent: Sep. 20, 2016

(54) SUTURE ANCHORING ASSEMBLIES AND METHODS OF USE

(75) Inventor: Lonnie E. Paulos, Pensacola Beach, FL (US)

(73) Assignee: THE LONNIE AND SHANNON PAULOS TRUST (AS AMENDED AND RESTATED), Salt Lake City, UT (US)

( * ) Notice: Subject to any disclaimer, the term of this patent is extended or adjusted under 35 U.S.C. 154(b) by 1066 days.

(21) Appl. No.: 13/405,320

(22) Filed: Feb. 26, 2012

(65) Prior Publication Data

US 2012/0158053 A1 Jun. 21, 2012

Related U.S. Application Data

(60) Continuation-in-part of application No. 13/241,466, filed on Sep. 23, 2011, now Pat. No. 8,512,377, which is a division of application No. 12/245,714, filed on Oct. 4, 2008, now Pat. No. 8,052,719.

(60) Provisional application No. 61/041,579, filed on Apr. 1, 2008.

(51) Int. Cl.
*A61B 17/04* (2006.01)
*A61B 17/00* (2006.01)
*A61B 17/06* (2006.01)

(52) U.S. Cl.
CPC .. *A61B 17/0401* (2013.01); *A61B 2017/00862* (2013.01); *A61B 2017/00986* (2013.01); *A61B 2017/0409* (2013.01);
(Continued)

(58) Field of Classification Search
CPC .......... A61B 17/0401; A61B 2017/00862; A61B 2017/0409; A61B 2017/06042; A61B 2017/0435; A61B 2017/0464; A61B 2017/00986; A61B 2017/0414; A61B 2017/0429; A61B 2017/0443; A61B 2017/0417
USPC ................. 606/139, 213, 215–217, 232–233
See application file for complete search history.

(56) References Cited

U.S. PATENT DOCUMENTS 5,002,550 A 3/1991 Li
5,041,129 A 8/1991 Hayhurst et al.
(Continued)

OTHER PUBLICATIONS

Kim Jun Gyu, International Search Report and Written Opinion for PCT Application PCT/US09/033615, Mailed Sep. 25, 2009, Korean Intellectual Property Office.
(Continued)

*Primary Examiner* — Gregory Anderson
*Assistant Examiner* — Son Dang
(74) *Attorney, Agent, or Firm* — John Brooks Law LLC; John J. Brooks, III

(57) ABSTRACT

A suture anchor assembly and methods of use will now are disclosed for the repair of human or animal tissue defects. The suture anchor assembly is capable of being inserted into a tissue or bone while also being able to create an expanded profile when subjected to a retrograde force. This expanded profile anchors the assembly into the tissue or bone by a changing of position of elements of the assembly relative to other assembly elements. Embodiments of the suture anchor assembly and methods are capable of precisely positioning assembly elements in the tissue or bone to effectively repair the defects. Some embodiments of the suture anchor assembly may include pliable buttons. And some embodiments of the suture anchor assembly may also include buttons made of bioabsorbable or resorbable materials.

20 Claims, 14 Drawing Sheets

(52) U.S. Cl.
CPC .......... *A61B 2017/0414* (2013.01); *A61B 2017/0417* (2013.01); *A61B 2017/0429* (2013.01); *A61B 2017/0435* (2013.01); *A61B 2017/0443* (2013.01); *A61B 2017/0464* (2013.01); *A61B 2017/06042* (2013.01)

(56) References Cited

U.S. PATENT DOCUMENTS

| | | | |
|---|---|---|---|
| 5,324,308 | A | 6/1994 | Pierce |
| 5,462,561 | A | 10/1995 | Voda |
| 5,545,178 | A * | 8/1996 | Kensey ............ A61B 17/0401 604/15 |
| 6,306,156 | B1 | 10/2001 | Clark |
| 6,592,610 | B2 | 7/2003 | Beyar |
| 6,626,916 | B1 | 9/2003 | Yeung et al. |
| 6,719,934 | B2 | 4/2004 | Stinson |
| 6,932,834 | B2 | 8/2005 | Lizardi et al. |
| 7,857,830 | B2 | 12/2010 | Stone et al. |
| 7,909,851 | B2 | 3/2011 | Stone et al. |
| 8,647,366 | B2 * | 2/2014 | Ken ............ A61B 17/0057 606/213 |
| 2002/0099258 | A1 * | 7/2002 | Staskin ............ A61B 17/3468 600/29 |
| 2002/0169477 | A1 | 11/2002 | Demopulos et al. |
| 2004/0015186 | A1 | 1/2004 | Bittar |
| 2004/0116963 | A1 * | 6/2004 | Lattouf ............ 606/224 |
| 2004/0260345 | A1 | 12/2004 | Foerster |
| 2005/0159762 | A1 | 7/2005 | Nuutinen et al. |
| 2005/0277983 | A1 | 12/2005 | Saadat et al. |
| 2006/0178680 | A1 | 8/2006 | Nelson et al. |
| 2006/0184202 | A1 | 8/2006 | Frazier et al. |
| 2006/0200177 | A1 | 9/2006 | Manzo |
| 2006/0206063 | A1 | 9/2006 | Kagan et al. |
| 2006/0217762 | A1 | 9/2006 | Maahs et al. |
| 2006/0235413 | A1 | 10/2006 | Denham et al. |
| 2006/0271073 | A1 | 11/2006 | Lam et al. |
| 2007/0010857 | A1 * | 1/2007 | Sugimoto ........ A61B 17/00234 606/232 |
| 2007/0032821 | A1 | 2/2007 | Chin-Chen et al. |
| 2007/0260259 | A1 | 11/2007 | Fanton et al. |
| 2008/0114399 | A1 | 5/2008 | Bonutti |
| 2008/0208252 | A1 * | 8/2008 | Holmes ............ 606/232 |
| 2009/0062850 | A1 * | 3/2009 | Ken ............ 606/215 |
| 2010/0268275 | A1 * | 10/2010 | Stone et al. ............ 606/232 |

OTHER PUBLICATIONS

International Bureau of the WIPO, International Preliminary Report on Patentability (IPRP) for related PCT App. No. PCT/US2009/033615, filed Feb. 10, 2009, IPRP Mailed Oct. 14, 2010, Switzerland.

* cited by examiner

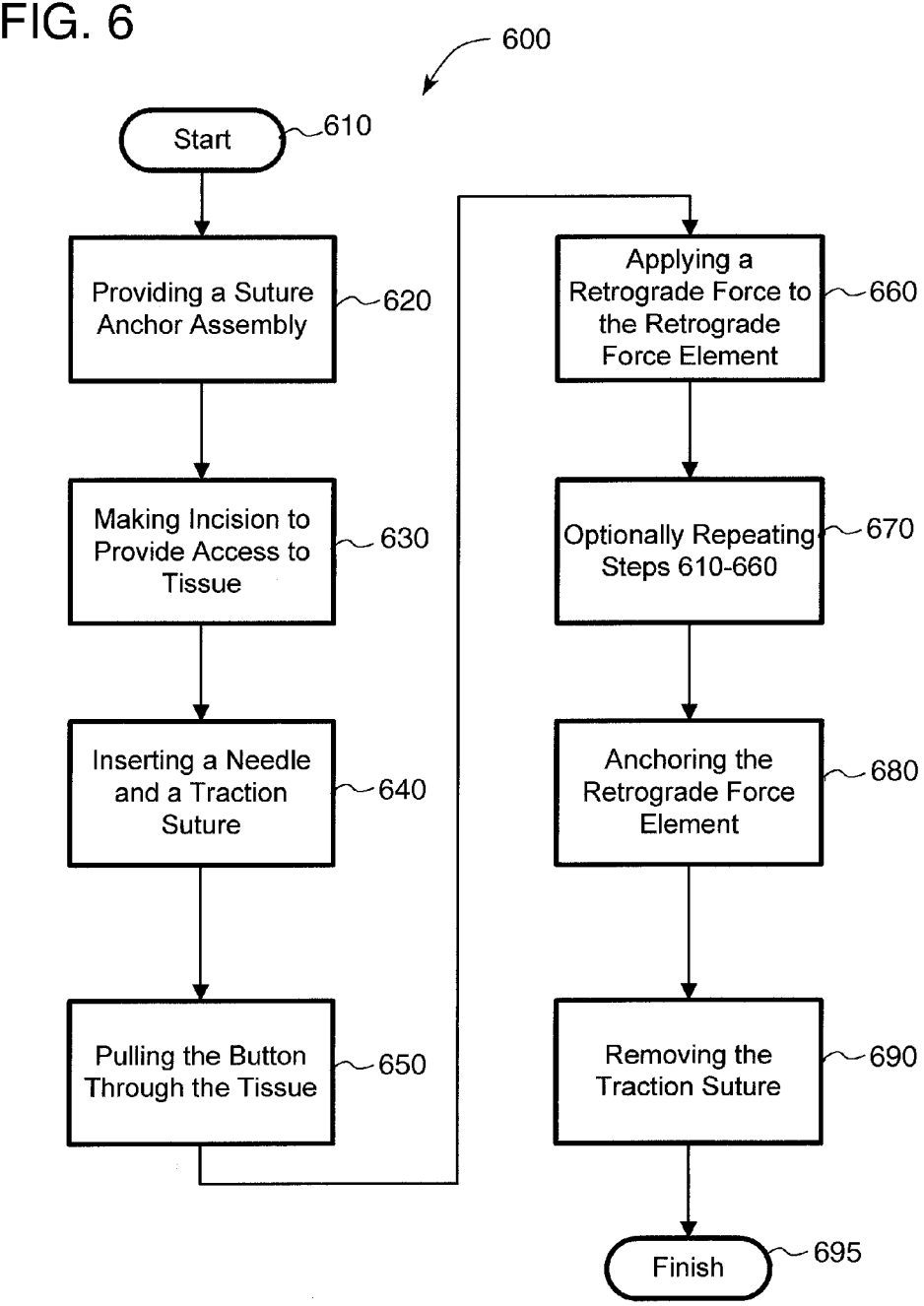

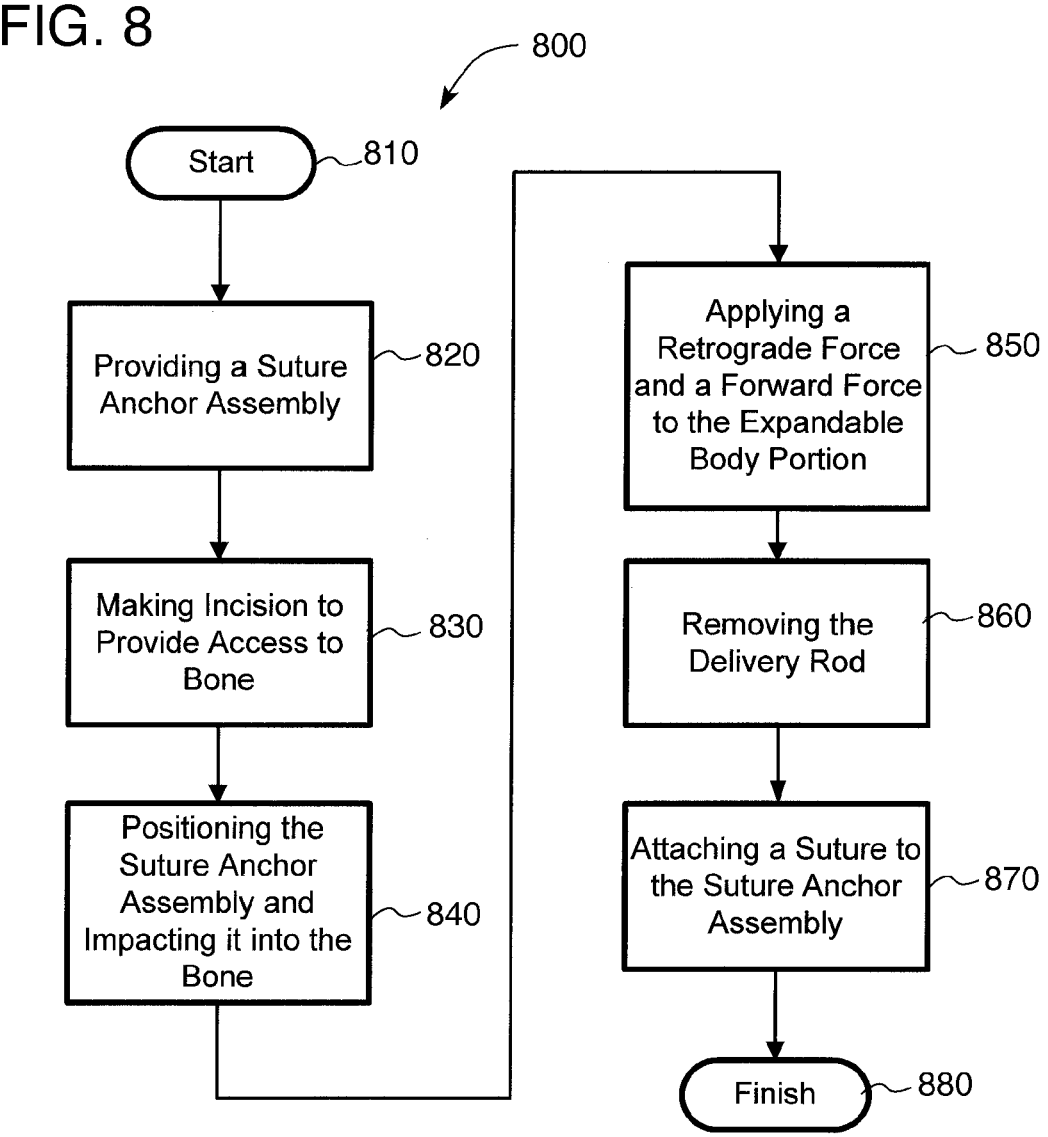

FIG. 10A
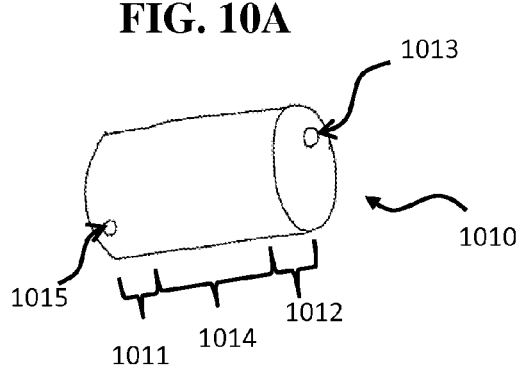
FIG. 10B
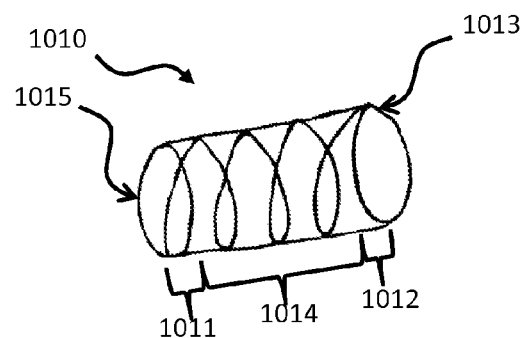
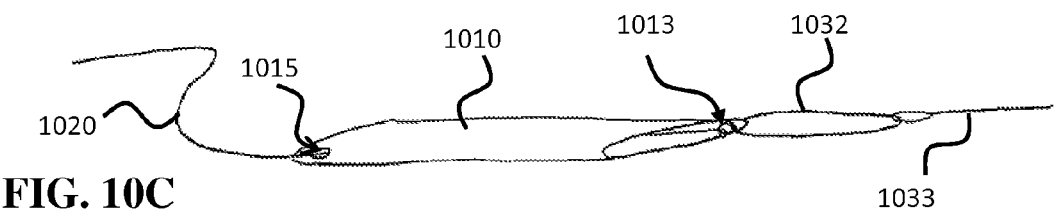
FIG. 10C
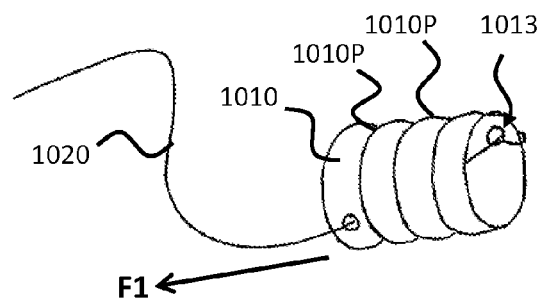
FIG. 10D
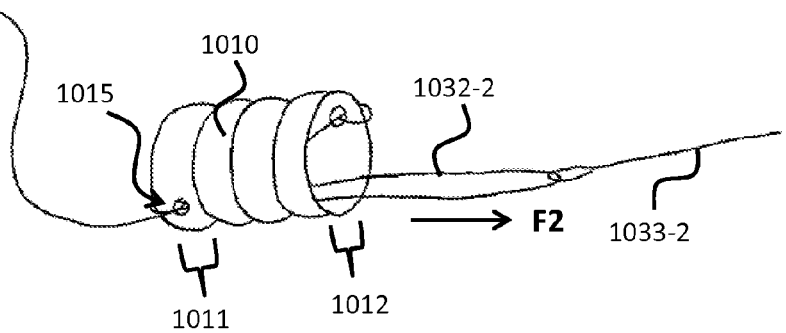
FIG. 10E

SUTURE ANCHORING ASSEMBLIES AND METHODS OF USE

CROSS-REFERENCE TO RELATED APPLICATIONS

This application is a continuation in part of U.S. patent application Ser. No. 13/241,466 filed Sep. 23, 2011 which is a divisional application of U.S. patent application Ser. No. 12/245,714 filed Oct. 4, 2008, now U.S. Pat. No. 8,052,719 issued Nov. 8, 2011, which claims benefit of U.S. Provisional Patent Application No. 61/041,579 filed Apr. 1, 2008, the entire contents of all referenced applications are incorporated herein by reference.

STATEMENT REGARDING FEDERALLY SPONSORED RESEARCH OR DEVELOPMENT

Not applicable

REFERENCE TO SEQUENCE LISTING, A TABLE, OR A COMPUTER PROGRAM LISTING COMPACT DISC APPENDIX

Not applicable

BACKGROUND OF THE INVENTION

1. Field of the Invention

The present invention relates generally to a systems and methods for securing sutures and other materials during surgical procedures. More particularly, embodiments of the present invention relate to systems and methods for suture fixation and methods designed for the placement of surgical anchors for the attachment of tissues associated with orthopedic surgeries. Embodiments of the present invention also relate to systems and methods designed to reduce, or bring into close approximation, pieces of torn or damaged soft tissue to facilitate tissue repair and healing.

2. Description of Related Art

Open and arthroscopic meniscal repair has become a mainstay for the orthopedic surgeon. In the 1960s and 70s partial or total mastectomy was the norm. As arthroscopy and arthroscopic skills advanced arthroscopic combined with open or all arthroscopic meniscal repair became the standard of care. Multiple studies have demonstrated the ability of the meniscus to heal, particularly in the vascular zone which is in the first 3 mm of its capsular attachment. With advancement of arthroscopic meniscal repair tools more and varying types of meniscal tears have been successfully repaired.

The present weaknesses of meniscal repair systems are several. First the gold standard has been the "inside out" meniscal repair system. With this method, cannulae are passed through skin portals, and use long needles with sutures attached that are passed through the cannulae, through the knee joint, across the defect and out of the knee to be retrieved through an open incision and then tied against the deep capsular structures away from neurovascular structures. This technique allows for precise placement of sutures in the meniscus.

One of the problems associated with these types of procedures is the time and number of intubations needed to perform the various procedures endoscipically. In addition, this technique does not allow for precise placement of sutures thru the capsule, and therefore there is potential for neurovascular injury.

The outside-in techniques involve passing sutures through needles at the joint line across the tear, and then tying one end of the sutures together and tying the other ends of the sutures directly onto the capsule. Alternative techniques allow the sutures to be passed across the defect and tying the suture back on itself on the capsule. One advantage to this technique is that there is a low risk of neurovascular injury, since needles are passed thru precise thru the capsule. Potential disadvantages of the outside-in technique is that suture placement thru the meniscus may not be precise as well as difficulty in reducing the defect and opposing the edges while passing the sutures.

In the past 15 years "all inside" devices have been developed for meniscal repair. These devices were developed in order to obviate the need for posterior corner incisions medial or lateral and to reduce the risk of neurovascular damage as a result of the surgery. These devices are deployed through the arthroscopic portals and either oppose the meniscal fragments and/or push a pre-tied knot onto the body of the meniscus. The present devices have created articular lesions due to protrusion as well as partially deployed devices that are proud.

Systems and methods such as that disclosed in U.S. Pat. Pub. No. 2006/0178680 Nelson et. al. illustrate some embodiments of an all-inside solution.

The all inside systems are limited by how accurate they are when repairing a meniscus and thus have never enjoyed as good a success rates as the inside out devices referenced above. Because the all inside devices are so large it is virtually impossible to accurately pass a suture and/or meniscal device into the under surface of the meniscus, thus the majority of the devices are passed on the top surface in an attempt to pinch the lower inferior portions together. This technique in actuality leaves the tear distracted on its inferior surface. Although many devices have been fabricated for all-inside meniscal repairs, which can be done endoscopically without the open-skin incision, the incidence of re-tear among patients who have undergone the procedure is higher over time compared with that for patients who were given inside-out permanent sutures There is a benefit therefore from providing a suture anchor assembly and methods of use that allow accurate placement of the suture and suture anchor. There is also a benefit from providing assemblies and methods that minimize the number of incisions required for use.

Bone Anchor Systems:

There are numerous bone anchors with sutures attached that allow tissues to be approximated to specific bone attachment sites. Most systems deploy a three-step system wherein the hole is drilled, anchor placed and then the anchor holder removed and the anchor set by pulling on sutures. If the bone is of questionable quality, the anchor may only temporarily hold and loosen later through the rehabilitation phases. Also, if the first step of drilling a hole can be eliminated then it would be expected that the anchor would hold more securely, particularly in porous bone.

Systems such as those disclosed in U.S. Pat. Pub. No. 2007/0032821, Chao et. al. and U.S. Pat. Pub. No. 2006/0217762 Maahs et. al. show anchor systems that expand into an opening, however, they are not structured to open into and secure an element in bone.

Other systems rely on an anchor to flip, based on a second suture being placed at the end opposite the attached suture. There are also systems that anchor by means of screwing in or anchoring by means of flexible hooks.

There is a therefore a benefit from providing a suture anchor assembly and method of use that can be easily inserted and deployed through expansion.

BRIEF SUMMARY OF THE INVENTION

The suture anchor assembly is an assembly that is capable of being inserted into a tissue or bone in a forward direction while also being able to create an expanded profile when subjected to a retrograde, or opposite direction, force. This expanded profile generally anchors and secures the assembly into the tissue or bone by a changing of position of elements of the assembly relative to other assembly elements. This changing of position creates an expanded profile of the assembly in the tissue which helps to frictionally engage the tissue and anchor the assembly. Embodiments of the assembly and methods of the present invention provide for the accurately positioning and of anchoring of elements to fix sutures in tissue or bone. In some embodiments, the suture anchor assembly has pliable elements and elements of the assembly are secured into the tissue by a deformation of assembly elements.

In an example embodiment, the suture anchor assembly comprises a first body portion, a second body portion having a force connector and a means to connect the first body portion and the second body portion whereby a retrograde force on the force connector causes the first body portion to engage a tissue and secure the suture anchor assembly in the tissue.

In an example embodiment, the suture anchor assembly includes the first and second body portions being planar shaped and the suture anchor assembly further includes a cannula having a slot shaped hollow portion to receive the planar body portions whereby the position of the first and second body portions can be controlled by the position of the slot shaped hollow portion.

In an example embodiment, the suture anchor assembly further comprises a needle, a means of connecting the needle to the first body portion and a retrograde force element capable of connecting to the second body portion force connector.

In an example embodiment, the suture anchor assembly further includes the first body portion being elongated, the means to connect the first body portion and the second body portion comprises a connector connecting a first connection point on the first body portion and a second connection point on the second body portion and the location of the force connector relative to the first body portion and the first connection point causes the first body portion to pivot relative to the second body portion when a retrograde force is applied to the force connector.

In an example embodiment, the suture anchor assembly further includes the first body portion being capable of compressing to form a front end and a expansion end and the expansion end of the first body portion being biased to expand whereby a retrograde force on the force connector cause the expansion end to expand and engage the tissue and secure the suture anchor assembly in the tissue.

In an example embodiment, the suture anchor assembly includes the first body portion being capable of being compressed to form a front end and a expansion end, the means to connect the first body portion comprising a collar on the first body portion to receive the second body portion and the expansion end of the first body portion being biased to expand whereby a retrograde force on the force connector forces the second body portion to expand the first body portion whereby the expansion end engages the tissue and secures the suture anchor assembly in the tissue.

In an example embodiment, the suture anchor assembly comprises an impactor, an expandable first body portion having a distal collar and a proximal collar and a second body portion having a force connector whereby a retrograde force on the force connector forces the second body portion against the distal collar and a forward force on the impactor transfers the forward force to the proximal collar whereby the first body portion expands to secure the suture anchor assembly in the tissue.

In an example embodiment, the suture anchor assembly further includes a delivery rod and a means to connect the delivery rod to the force connector whereby a force applied to the delivery rod is transferred to the second body portion.

In an example embodiment, the suture anchor assembly further includes a means to retain the expansion of the first body portion to secure the suture anchor assembly in the tissue.

In an example embodiment, the suture anchor assembly comprises a pliable button with a first body portion and a second body portion whereby a retrograde force on a force connector causes the pliable button to deform and engage a tissue and secure the pliable button in the tissue.

In some embodiments, the button is resorbable or bioabsorbable.

In some embodiments, the button is deformed by a forward force on the button which causes the button to deform and engage the tissue and secure the button in the tissue.

In an example embodiment, a method of tissue repair comprises providing a suture anchor assembly having a retrograde suture, inserting the suture anchor assembly into a tissue, applying a retrograde force on the retrograde force element to cause the suture anchor assembly to engage the tissue and secure the suture anchor assembly in the tissue and anchoring the retrograde force element to secure the suture anchor assembly.

In an example embodiment, the step of inserting a suture anchor assembly further includes inserting a needle connected to the suture anchor assembly and passing the needle and suture anchor assembly through the tissue.

In an example embodiment, the suture anchor assembly further includes a first body portion connected to a second body portion connected to the retrograde suture and the step of applying a retrograde force on the retrograde force element further includes causing the first body portion to engage the tissue.

In an example embodiment, the suture anchor assembly is planar and further comprises a cannula having a slot shaped hollow portion to receive the planar suture anchor assembly and the step of inserting the suture anchor assembly further includes positioning the insertion of the planar anchor assembly by the position of the slot shaped hollow portion.

In an example embodiment, the method of tissue repair further includes repeating the step of inserting the suture anchor assembly and applying the retrograde force with at least one second suture anchor assembly having a second retrograde suture and the step of anchoring the retrograde force element further comprises anchoring the retrograde force element to the second retrograde force element to secure the suture anchor assemblies.

In an example embodiment, the step of inserting a needle includes inserting the needle through a cannula.

In an example embodiment, the first body portion is elongated and the step of applying a retrograde force to the retrograde force element causes the elongated first body portion to pivot relative to the second body portion and engage the tissue.

In an example embodiment, the first body portion is capable of being compressed to form a front end and an expansion end, the expansion end of the first body portion expands when not compressed and the step of applying a retrograde force on the retrograde force element includes causing the expansion end to expand and engage the tissue.

In an example embodiment, the first body portion is capable of being compressed to form a front end and a expansion end, the first body portion is connected to the second body portion by a collar on the to receive the second body portion, the expansion end of the first body portion expands when not compressed and the step of applying a retrograde force on the retrograde force element includes forcing the second body portion to expand the first body portion where the expansion end expands and engages the tissue.

In an example embodiment, a method of anchoring a suture into a tissue comprises providing a suture anchor assembly with an expandable first body portion, a second body portion and a force connector connected to the second body portion; inserting the expandable first body portion and second body portion of a suture anchor assembly into a tissue; expanding the first body portion of the suture anchor assembly by applying a retrograde force to the force connector to secure the suture anchor assembly in the tissue; and attaching a suture to the suture anchor assembly.

In an example embodiment, the step of inserting the second body portion further includes applying a first forward force on a sharpened distal end of the second body portion and the step of expanding the first body portion further includes applying the retrograde force to a distal end of the first body portion and applying a second forward force on a proximal end of the first body portion expanding the first body portion.

In an example embodiment the step of expanding the first body portion further includes applying the retrograde force by forcing a wedge shaped proximal end of the second body portion into a collar of the distal end of the first body portion and applying the second forward force with an impactor whereby the retrograde force and the second forward force expands the outer dimension of the first body portion.

BRIEF DESCRIPTION OF THE SEVERAL VIEWS OF THE DRAWINGS

FIG. 6. A process diagram outlining one embodiment of the method of operating on embodiment of the suture anchor assembly.

FIG. 8. A process diagram outlining one embodiment of the method of operating on embodiment of the suture anchor assembly.

FIG. 10A. A perspective view of an example embodiment of a tubular shaped button.

FIG. 10B. A perspective view of an example embodiment of a button shaped from a mesh material.

FIG. 10C. A perspective view of an example embodiment of a tubular button as it may be collapsed in an insertion profile when used with a needle, a traction suture and a suture as inserted through a tissue.

FIG. 10D. A perspective view of an example embodiment of a tubular shaped pliable button as it may be deformed upon receiving a retrograde force.

FIG. 10E. A perspective view of an example embodiment of a tubular button as it may be deformed upon receiving a forward force.

DETAILED DESCRIPTION OF THE INVENTION

A suture anchor assembly and methods of use will now be described in detail with reference to the accompanying drawings. Although embodiments are described for the repair of meniscal defects, it is understood that the methods and systems described can be use for the repair of other human or animal body defects. In particular it is contemplated that other embodiments of the invention can be use for repair and suture anchoring to bone or other tissues. Notwithstanding the specific example embodiments set forth below, all such variations and modifications that would be envisioned by one of ordinary skill in the art are intended to fall within the scope of this disclosure.

Throughout this description, a retrograde force means a force applied generally opposite of the direction of insertion of the assembly. Additionally, the verbs anchor and secure as used throughout this description mean to hold fast or otherwise fix or fasten.

Figure 1:
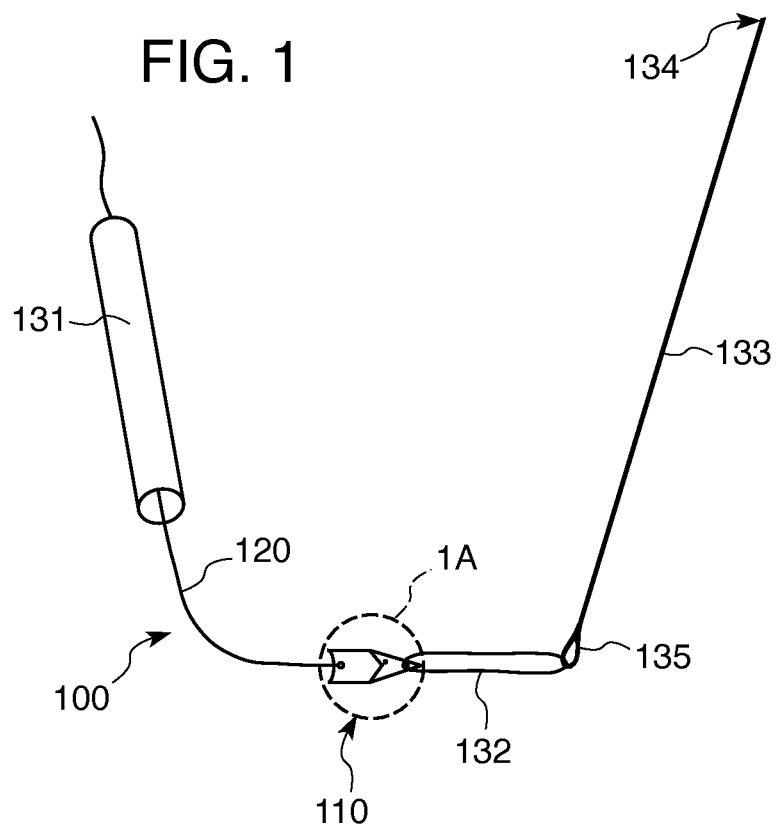
FIG. 1. A top view of one embodiment of the suture anchor assembly.

Suture Anchor Assembly:

One embodiment of the suture anchor assembly is shown in FIG. 1. The suture anchor assembly 100 shown and described is a device that provides elements to allow new combinations of some features of the "inside-out" and "all-inside" solutions. This solution takes advantage of the accuracy and reliability of inside-out and outside-in suture solutions but can result in a device with all-inside features once the system has been deployed. Thus, by using this assembly outside incisions can be minimized while the accuracy and effectiveness of the inside-out system can be duplicated.

The assembly disclosed provides a solution that can be accurately placed around the defect, can be placed with fewer incisions and can be positioned to reduce the incidence of protrusions that may irritate the tissue or bone around the defect.

As shown in FIG. 1, one embodiment of the suture anchor assembly 100 comprises at least one set of a retrograde force element 120, a button 110 and a delivery system.

The retrograde force element 120 is connected to the button 110 by a force connector 113. The retrograde force element 120 is used to deploy and anchor the button 110. As shown in FIG. 1, the retrograde force element 120 may comprise a retrograde suture that provides the retrograde force and also secures that suture and anchor pair to another suture/anchor pair so that the defect is repaired or reinforced. Any type of surgical suture is suitable for use as a retrograde suture with this assembly. It is also understood that other types of retrograde force elements can be used to deploy the anchor and secure assembly elements and tissue together. These other types of retrograde force elements may include, but not be limited to other securing elements such as rods, pins, staples and other materials that can transfer and maintain a tensile force.

Figure 1A:
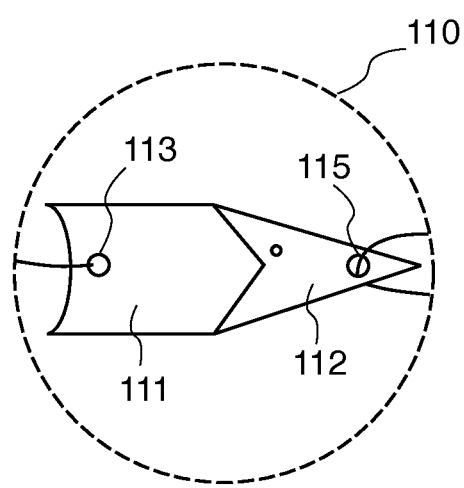
FIG. 1A. A top view of one embodiment of a button.

As detailed in FIG. 1A, the button 110 is a rigid or semi-rigid element with a force connector 113. The button 110 is shaped to change or transform shape when a retrograde force is applied to the force connector 113. Although not required, this transformation can be done with some degree of control of the profile of the button. This change of shape allows the button 110 to anchor in the tissue and counter that same, or a different retrograde force. The button 110 can be made of biocompatible materials that include, but are not limited to metals, metal alloys or non-metallic materials such as nylon, polyethylene, polypropylene or any combination thereof. The force connector 113 provides the connection through which forces are transferred to the button 110. Although shown in this embodiment as a suture tie for the retrograde suture, the force connector 113 can comprise any element capable of connecting the retrograde force element to the button in a way that a tensile force can be applied and maintained on the force element. Suitable connection elements include, but are not limited to mating threads, clips, hooks, holes, permanent adhesive connections or any combination thereof.

Figure 2A:
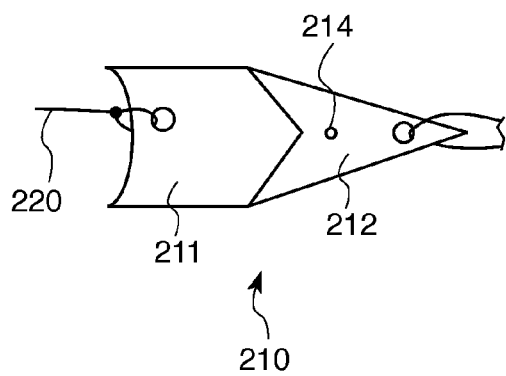
FIGS. 2A-2D. A top view of multiple embodiments of the button in an insertion and deployed position.
Figure 2B:
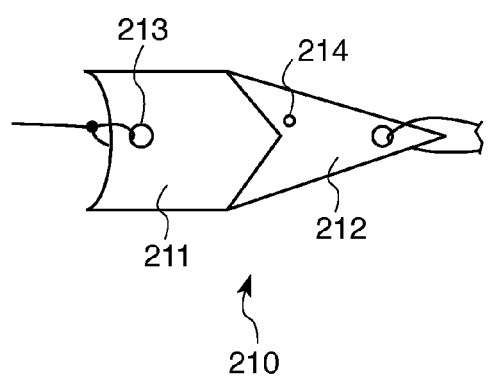
Figure 2C:
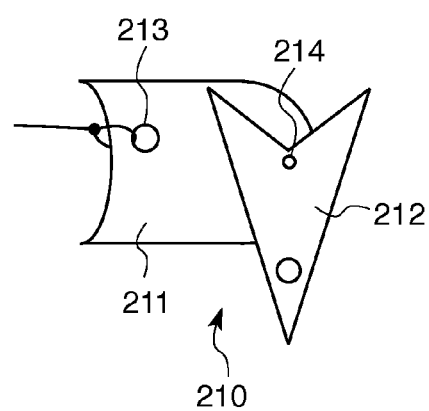
Figure 2D:
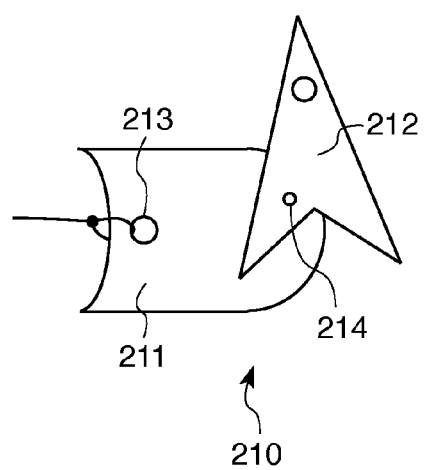

In the embodiment shown in FIGS. 2A-2D, the button 210 comprises an expandable first body portion 212 and second retrograde force body portion 211 and a means to connect the two portions. In this embodiment, the expandable body portion 212 is a generally elongated and pointed section and the retrograde force body portion 211 is generally a broad section. The expandable and retrograde force portions each have a connection point and are connected to each connection point by a connector 214. The connection points comprise a means of receiving a connector such as a hole, slot or adhesive and the connector comprises a means of connecting the two body portions such as, but not limited to a pivot hinge or rivet. The retrograde force element in this embodiment comprises a retrograde suture 220. The retrograde suture 220 is connected to the retrograde force portion 211 of the button through the force connector comprising a suture tie 213. This suture tie 213 can be any method of securing a suture to the body portion. The suture tie as shown in FIGS. 2A 2D comprises an off-center hole in the retrograde force portion 211.

The means to connect the body portions of the button can include any connecting methods that allow the two portions to pivot and/or rotate about the connection points. For example, it is contemplated that the connector 214 may be comprised of a protrusion, hook or other connection element on one body portion that is capable of being connected to a complementary hole, slot or other connecting element on the other body portion.

The interoperation of the suture tie 213, the connection points and the two button body portions are such that a retrograde force on the suture tie urges the expandable body portion 212 to rotate or otherwise move in a direction at an angle different than the retrograde force. This rotation or movement causes an expanded profile of the button which frictionally increases the resistance that can be provided by the button and expansion suture. The elongated shape, where the length of the portion in an insertion position is greater than its width, of the expandable body portion causes this expanded profile when the expandable portion is moved about the connector. This interoperation to cause the expandable body portion to rotate can be provided by a location of the suture tie relative to the connection points. One example of this interoperation is shown in FIG. 2A where the location of suture tie 213 is off the center of the retrograde force body portion 211 while the connector 214 and connection point is located in the center of both button portions. As shown in FIG. 2B, a retrograde force on the suture tie 213 cause a force on the connector 214 that causes the expandable body portion 212 to pivot and/or rotate at an angle different than the direction of the retrograde force. Alternately, as shown in FIGS. 2C-2D, the location of the connection points on the expandable body portion to be off-center while the suture tie is on the center line of the body portion.

It is also contemplated to have the shape of the body portions such that a retrograde force on the button causes the expandable body portion 212 to pivot and/or rotate. For example, the expandable body portion can have a barb or other protrusion on its expansion end that causes that portion to rotate when partially retracted by the application of a retrograde force.

In some embodiments, the shape of the button can be made such that it minimizes the possibility of undesired protrusions when the button is deployed. An undesired protrusion is a protrusion that can damage other tissues or bone. These undesired protrusions are different than the desired protrusions caused the normal expansion of the button. For example, as in FIGS. 2A-2D, the shape of the button can be made so that it is primarily a two-dimensional planar shape with a minimal profile in a third dimension. This allows the button to be inserted and to expand primarily in dimensions parallel to particular surfaces, such as the articular cartilage surfaces of the knee, while minimizing the potential for expanding perpendicular to those surfaces. This minimizes the possibility of having protrusions that may damages these surfaces or tissues. It is also contemplated that the shape of the cannula can be made to assist in the positioning of the button in deployment. This can be provided by, but not limited to an inner bore shape of the cannula that is primarily slot shaped to cooperate with a primarily two-dimensional shaped button. This would allow the profile of the button in the tissue to be controlled by the rotational position of the cannula. Other cooperating shapes of button and cannula bores are contemplated such as ovals, circles and rectangles.

Referring back to the embodiment shown in FIG. 1, the suture anchor assembly also comprises a delivery system for the button 110 and retrograde force element 120. As shown in the embodiment in FIG. 1, this delivery system comprises a needle 133, a traction suture 132 and a cannula 131.

The needle 133 is used to position and insert the button 110 and retrograde force element 120. The needle 133 comprises an elongated rod with a sharpened distal end 134 and a proximal end 135 that has an eye or other means to allow connection to the traction suture 132. As an example, and not for limitation, 12 inch long needles made of stainless steel or Nitinol are suitable for use with this assembly.

The traction suture 132 is connected to the needle's proximal end 135 and the button 110. Preferably, the traction suture is connected to a traction suture tie 115 on the sharpened end of button's expandable body portion 112. The traction suture 132 is used to connect the needle 133 and the button 110 allowing the button to be pulled through the tissue and the defect to be deployed on one side of the defect. Any type of surgical suture or similar connection means is suitable for use as a traction suture with this assembly.

The retrograde force element 120 is connected to the force connector 113 on a retrograde force body portion 111 of the button 110.

The cannula 131 is used to help position and deploy the needle 133. The cannula 131 is a hollow element with a longitudinal extending bore to receive the needle, the traction suture, the button and the expansion suture. As an example, and not for limitation, 6 inch hollow cannula of about ⅜ inch in diameter is suitable for use with this assembly. In one embodiment, the distal end of the cannula is bent at angles to help guide the needles into the proper direction and position.

And although the delivery system embodiment described includes a traction suture connected to a traction suture tie and the eye of a needle, other means to connect the needle and the button are contemplated that include flexible, semi-flexible or substantially rigid connecting elements. Examples of these connecting elements include but are not limited to a directly mating connection between the needle and the button such as a threaded connection, one element hooking into an eye of another or one element clipping into a recess of another. Other examples of connecting elements include, but are not limited to a connector connecting the needle and the button such as a flexible hook, chain, wire, rods or other means to removeably connect the two elements.

Alternative Button Embodiments

Alternative embodiments of the button are shown in FIGS. 3A-5B.

Figure 3A:
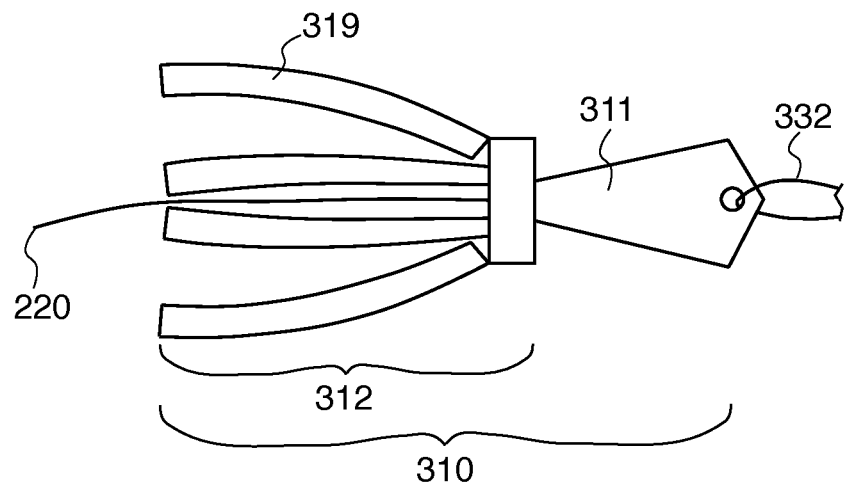
FIGS. 3A-3B. A top view of one embodiment of the button in an insertion and a deployed position.
Figure 3B:
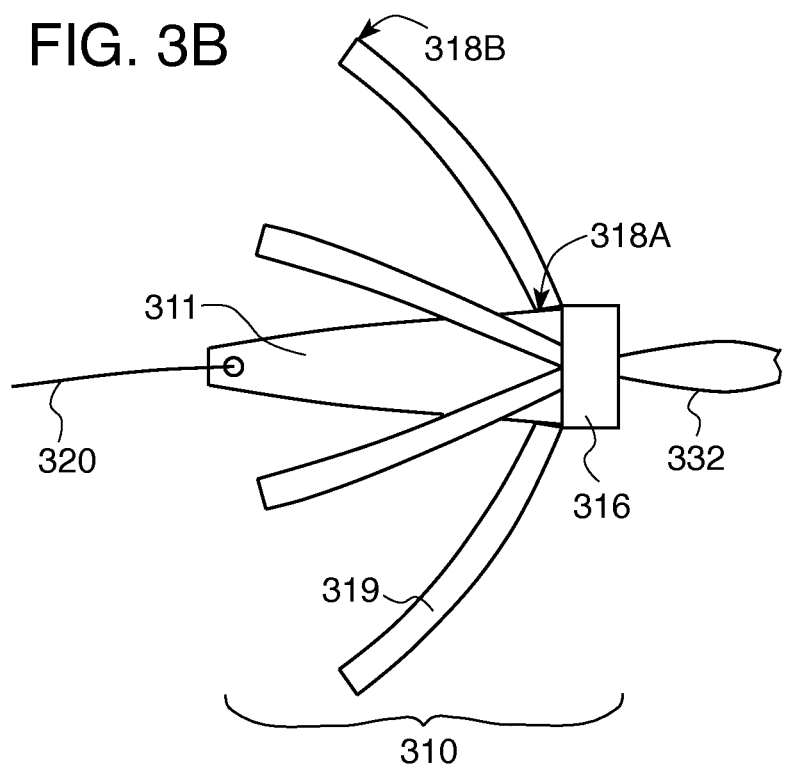

FIGS. 3A and 3B illustrate one embodiment of the button 310. In the illustrated embodiment, the button 310 comprises an expandable first body portion 312 comprising expansion fingers 319, a collar 316 and a retrograde force body portion 311 that is shaped as a rod. The retrograde force body portion 311 is connected to both the traction suture 332 and the retrograde suture 320 (retrograde force element) and is received into a collar 316. As shown in FIG. 3A, this embodiment is able to be inserted into a patient's body starting with the traction suture end. In the insertion position of FIG. 3A, the fingers are compressed to minimize the profile of the assembly during insertion. When sufficient tension is placed on the retrograde force body portion 311 from the retrograde suture side, the retrograde force body portion 311 retracts towards the expandable body portion 312 and into the collar 316, deploying the expansion fingers 319. The expansion fingers 319 engage the retrograde force body portion 311 so that the fingers are urged to expand when the rod retracts. As shown in FIG. 3B, the fingers have an angled end 318A on the end that connects with a collar 316. When the retrograde force body portion 311 is retracted, this angled end 318A is rotated about a connection to the collar 316 forcing the expansion ends 318B of the fingers 319 to expand. Other methods of cooperation between the fingers and the retrograde force rod so that the fingers expand are contemplated to include any types of angles for the angled end 318A and any type of tethered connection to the collar that allows the fingers 319 to move and expand.

As shown in FIG. 3B, the deployment of the fingers 319 enables the button 310 to act as an obstruction and anchor for the retrograde suture 320 connected to the button.

Figure 4A:
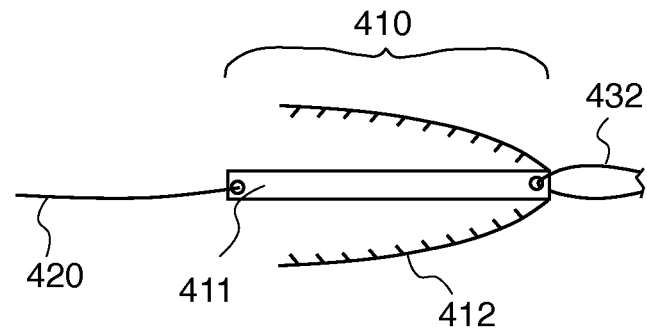
FIGS. 4A-4B. A top view of one embodiment of the button in an insertion and a deployed position.
Figure 4B:
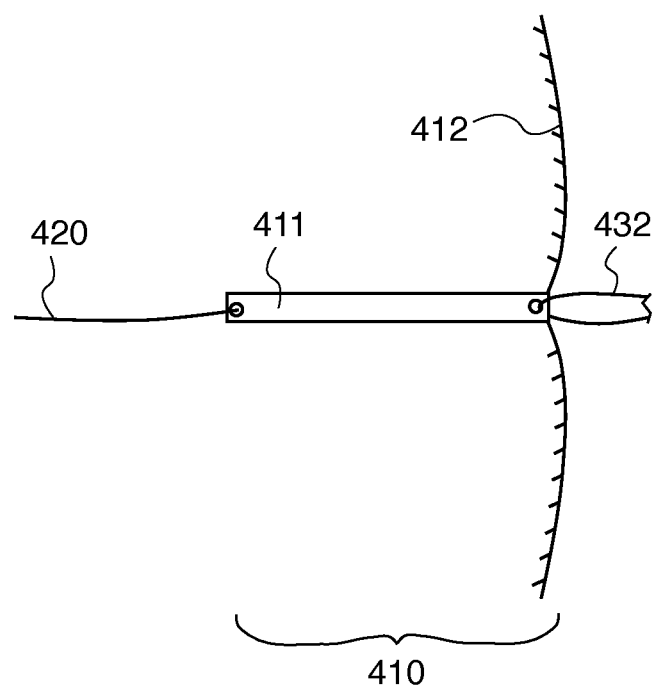

FIGS. 4A and 4B illustrate another embodiment of a button 410. In the illustrated embodiment, the button comprises an expandable first body portion 412 comprising a flexible hoop that is biased to expand and a second retrograde force portion 411 shaped like a bar. The retrograde force body portion 411 is connected to the traction suture 432 and the retrograde suture 420. As shown in FIG. 4A, this embodiment is able to be inserted into a patient's body starting with the traction suture end and the flexible hoop is folded back, or otherwise compressed against its bias to expand and to minimize its profile during insertion. When compressed, the end of the flexible hoop nearest the traction suture is the front end and the opposite end of the hoop is the expansion end. When placed in position, the expandable body portion 412 is expanded about its front end by a trip or by the release of tension on the hoop. As shown in FIG. 4B, the expansion and deployment of the expansion end of the expandable body portion 412 enables the button 410 to engage the tissue and act as an obstruction and anchor for the retrograde suture connected to the button 410.

Embodiments of the buttons may include rigid buttons made of rigid bioabsorbable or resorbable materials such as but not limited to polyglycolic acid, polylactic acid enantiomers, poly-D-L-lactic acid copolymer polyglycolic acid, a combination of polylactic acid and hydroxyapatite or materials such as collagen.

Embodiments of buttons may also include pliable buttons made of soft or pliable material or a rigid material configured, such as a rigid material configured as a spring-like spiral or a woven mesh, to bend, fold, dilate, expand or otherwise deform upon application of a force on the button. Embodiments of pliable buttons may be made of bioabsorbable, resorbable or non-resorbable materials. For illustration only, and not for limitation, embodiments of a pliable button may be made of materials including braided sutures, sponges and sponge-like materials in solid form, perforated materials, woven/braided from biocompatible materials or fibers, such as, for example, polymer, polyester, polyethylene, cotton, silk, or other natural or synthetic materials, including sponges and sponge-like materials. The button may also be an elongated tubular or solid member or a two-dimensional member with or without internal bores. The button may have any properties that allow it to change shape. The button can be, for example, compliant, flexible, foldable, squashable, squeezable, deformable, limp, flaccid, elastic, low-modulus, soft, spongy, perforated or have any other flexible properties which allow it to change shape.

The pliability of the button allows the button to deform upon application of a force. The deformation may be any change in shape that helps the button become more secured in the tissue. For example, the deformation may be to extend, swell, enlarge, expand, widen, dilate, distend, inflate or become larger and taking up more space in a dimension that helps secure the button.

Two example embodiments of a generally tubular shaped pliable button are shown in FIGS. 10A and 10B. FIG. 10A illustrates a tubular sleeve shaped button 1010 having a first body portion 1012 and a second body portion 1011. In this embodiment, the force connector 1013 is on the first body portion 1012. The first body portion 1012 also has a means to connect the first body portion 1012 with the second body portion 1011 whereby a retrograde force on the force connector 1013 causes the button 1010 to deform and engage a tissue and secure the button 1010 in the tissue. In this embodiment, the means to connect the body portions is a middle body portion 1014 which is a continuation of the tubular sleeve between the two body portions and the force connector 1013 is a through hole extending through the wall of the button 1010. FIG. 10C illustrates one embodiment of a suture anchor assembly having a button 1010, a traction suture 1032, a needle 1033 and a suture 1020. The means to connect the needle to the first body portion by a suture tie which in this embodiment also functions as the force connector 1013. This illustration shows the assembly in a collapsed, insertion profile as it may look while being inserted and pulled through a tissue by the needle 1033 and traction suture 1032. FIG. 10D illustrates the embodiment of FIG. 10C with the traction suture and needle removed and a retrograde force F1 being applied to the suture 1020 and the force connector 1013. In this embodiment, the suture 1020 is the retrograde force element and it extends through a longitudinal inner bore of the button through a foot connector 1015. As shown, the button 1010 is deformed into a dilated anchor profile shape that helps anchor the button in the tissue. As can be seen, the foot connector 1015 is also shown which can retain the second body portion 1011 in relation to the first body portion 1012 so that the button 1010 resists eversion (e.g. inverting or "flipping inside out") as the retrograde force is applied. In this embodiment, the foot connector 1015 is a through hole extending through the wall of the second body portion 1011 of the button 1010 and the foot connector 1015 is sized similar to the force connector 1013 so that it restricts the movement of the second body portion 1011 with respect to the first body portion 1012 to resist the button 1010 inverting or everting. As can also be seen, protrusions 1010P may also be formed in the deformation that helps the button 1010 engage the tissue.

FIG. 10B illustrates one embodiment of a button 1010 comprising a generally pliable weave or mesh tube. In some embodiments, the mesh button can be a self-expanding button designed similar to self-expanding stents described in U.S. Pat. No. 6,719,934 issued Apr. 13, 2004 to Jonathan S. Stinson which is herein incorporated by reference in its entirety. These weave or mesh embodiments may incorporate the other elements of buttons such as the force connector 1013, foot connector 1015 as well as the first body portion 1012, second body portion 1011 and the middle body portion 1014. Here the force connector 1013 and the foot connector 1015 can be portions of the mesh, or special loops in the mesh, that can be used to secure elements such as sutures.

FIG. 10E illustrates additional elements that may be used with the pliable button embodiments. As shown, this example suture anchor assembly has a second suture 1032-2 extending through the button 1010 and connected to the second body portion 1011, here at the foot connector 1015, and a second needle 1033-2. This second suture 1032-2, as a forward force element, is able to apply a forward force F2 on the second body portion through the foot connector 1015. This forward force F2, with or without an opposite retrograde force on the force connector, causes the button 1010 to deform into a dilated anchor profile shape that anchors the button 1010 into the tissue. In this embodiment, the deformation occurs closer to the position of the first body portion 1012 which may be helpful in positioning the button.

Figure 11A:
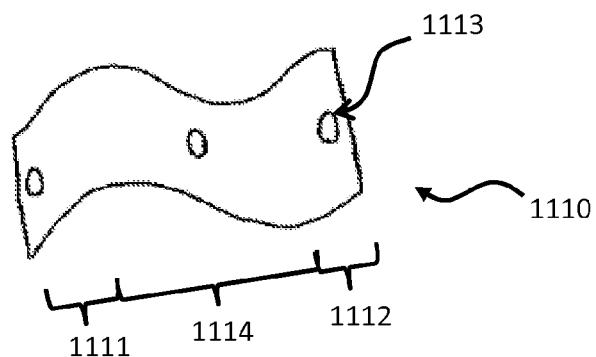
FIG. 11A. A perspective view of an example embodiment of a pliable sheet as a button.
Figure 11B:
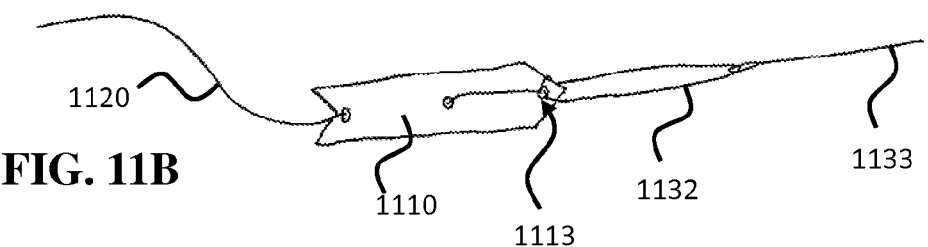
FIG. 11B. A perspective view of an example embodiment of a pliable sheet as a button as it may be collapsed in an insertion profile when used with a needle, a traction suture and a suture as inserted through a tissue.
Figure 11C:
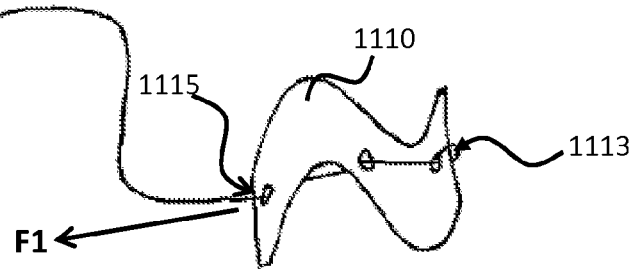
FIG. 11C. A perspective view of an example embodiment of a pliable sheet as a button as it may be deformed upon receiving a retrograde force.

FIGS. 11A-11D illustrates another embodiment of a pliable suture anchor assembly. As shown in FIG. 11A, this embodiment has a button 1110 comprising a pliable generally planar sheet. This button 1110 has a first body portion 1112 and a second body portion 1111. The first body portion 1112 has a force connector 1113 and has a means to connect the first body portion 1112 with the second body portion 1111 whereby a retrograde force on the force connector 1113 causes the pliable button 1110 to deform and engage a tissue and secure the button in the tissue. In this embodiment, the means to connect the body portions is a middle body portion 1114 is a continuation of the sheet between the two body portions and the force connector 1113 is a through hole extending through the button. FIG. 11B illustrates one embodiment of the suture anchor assembly having a button, 1110, a traction suture 1132, a needle 1133 and a suture 1120 connected to the first body portion by a suture tie which in this embodiment is also the force connector 1113. The traction suture 1132 provides the means to connect the needle with the suture tie and the first body portion. This illustration shows the assembly in a collapsed, insertion profile as it may look being inserted and pulled through a tissue by the needle 1133 and traction suture 1132. FIG. 11C illustrates the embodiment of FIG. 11B with the traction suture and needle removed and a retrograde force F1 being applied to the suture 1120, as the retrograde force element, and the force connector 1113. As shown, the button 1110 is deformed into a dilated or folded anchor profile shape that helps anchor the button 1110 in the tissue. As can be seen, a foot connector 1115, here a through hole, is also shown which can retain the second body portion in relation to the first body portion so that the button resists eversion as the retrograde force is applied. In this embodiment, the foot connector 1115 is sized similar to the force connector 1113 so that it restricts the movement of the second body portion with respect to the first body portion and helps the button resist everting. In some embodiments, as shown, the retrograde force element is interwoven through multiple through holes, or foot connectors, along sections and alternating sides of the button which promotes dilated deformation and further preventing the button from everting.

Figure 11D:
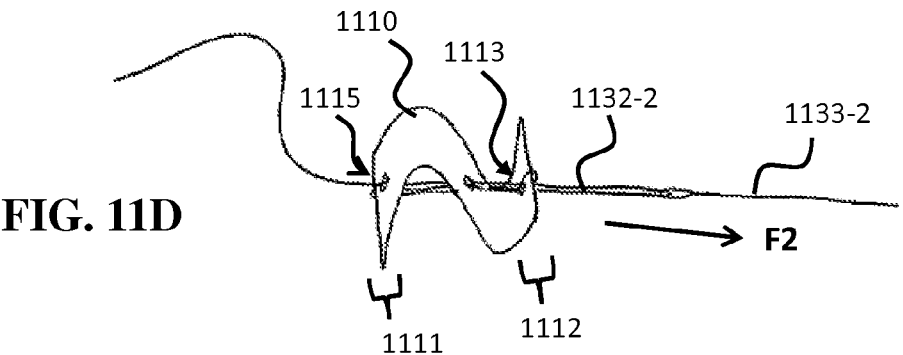
FIG. 11D. A perspective view of an example embodiment of a pliable sheet as a button as it may be deformed upon receiving a forward force.

FIG. 11D illustrates one embodiment where the anchor assembly further comprises a second suture 1132-2 extending through the button and connected to the second body portion 1111, here at the foot connector 1115, and a second needle 1133-2. This second suture 1132-2 as the forward force element is able to apply a forward force F2 on the second body portion 1111 through the foot connector 1115. This forward force F2, with or without an opposite retrograde force on the force connector 1113, causes the button 1110 to deform into a dilated shape that anchors the button 1110 into the tissue. In this embodiment, the deformation occurs closer to the position of the first body portion 1112 which may be helpful in positioning the button.

Figure 12A:
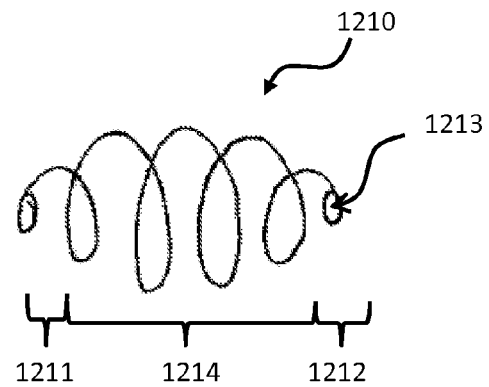
FIG. 12A. A perspective view of an example embodiment of a spiral shaped button.
Figure 12B:
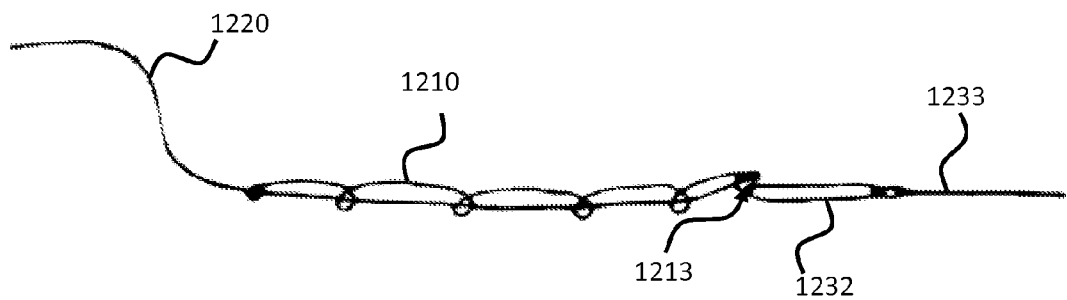
FIG. 12B. A perspective view of an example embodiment of a spiral shaped button as it may be collapsed in an insertion profile when used with a needle, a traction suture and a suture as inserted through a tissue.
Figure 12C:
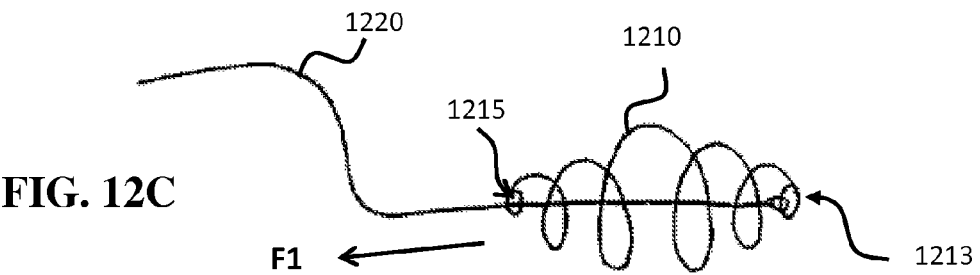
FIG. 12C. A perspective view of an example embodiment of a spiral shaped button as it may be deformed upon receiving a retrograde force.

FIGS. 12A-12C illustrates another embodiment of a pliable suture anchor assembly. As shown in FIG. 12A, this embodiment has a button 1210 comprising a pliable, generally spiraled or coiled element. This button 1210 has a first body portion 1212 and a second body portion 1211. The first body portion 1212 has a force connector 1213 and has a means to connect the first body portion 1212 with the second body portion 1211 whereby a retrograde force on the force connector causes the button 1210 to deform and engage a tissue and secure the suture anchor assembly in the tissue. In this embodiment, the means to connect is a middle body portion 1214 which is a winding of the coiled element between the two body portions and the force connector 1213 is a closed loop in the first body portion 1212 of the button. FIG. 12B illustrates one embodiment of the suture anchor assembly having a button 1210, a traction suture 1232, a needle 1233 and a suture 1220 connected to the first body portion by a suture tie which in this embodiment also functions as the force connector 1213. The traction suture 1232 provides the means to connect the needle with the suture tie and the first body portion. This illustration shows the assembly in a collapsed insertion profile as it may look being inserted and pulled through a tissue by the needle 1233 and traction suture 1232. FIG. 12C illustrates the embodiment of FIG. 12B with the traction suture and needle removed and a retrograde force F1 being applied to the suture 1220 (retrograde force element) and the force connector 1213. As shown, the button 1210 is starting to deform into a dilated anchor profile shape that helps anchor the button in the tissue. As can be seen, a foot connector 1215 is also shown which can be shaped to help resist eversion of the button 1210 as the retrograde force F1 is applied. Similar to the above embodiments, this embodiment may have a second suture connected to the foot connector 1215 that can be used as a forward force element to deform the button 1210 with a forward force.

Figure 13A:
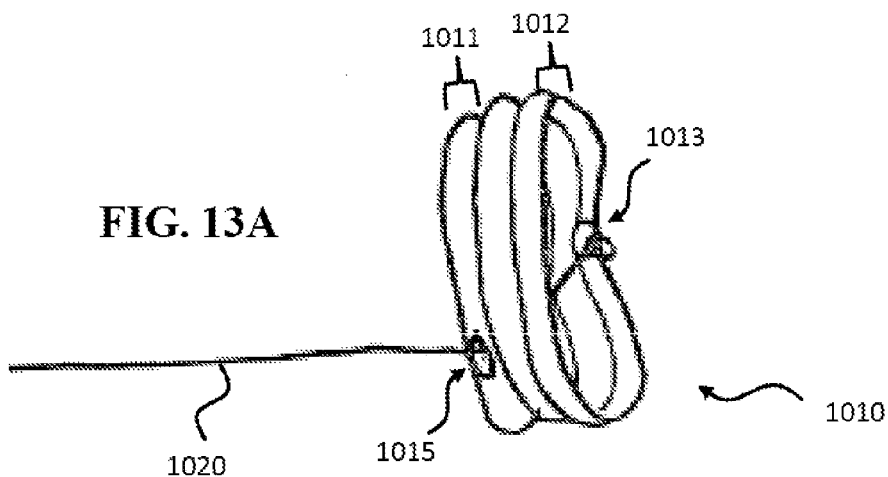
FIG. 13A. A perspective view of the example embodiment of the button of FIG. 10A in a dilated anchor profile.
Figure 13B:
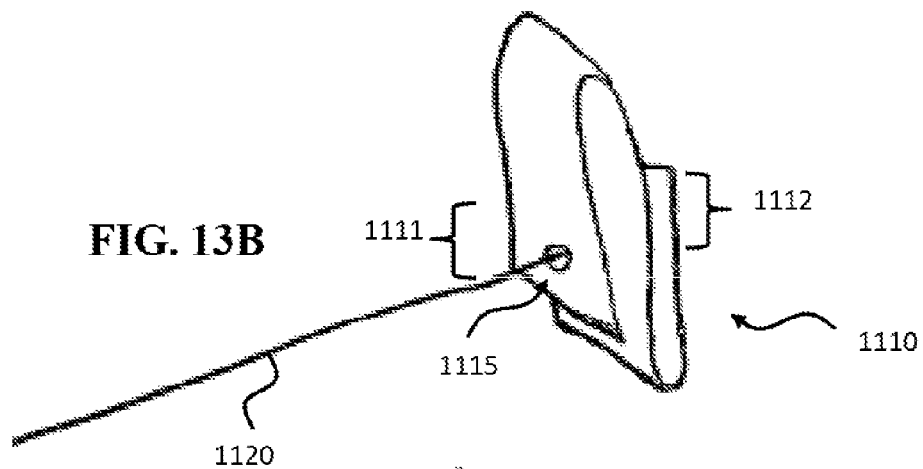
FIG. 13B. A perspective view of the example embodiment of the button of FIG. 11A in a folded anchor profile.
Figure 13C:
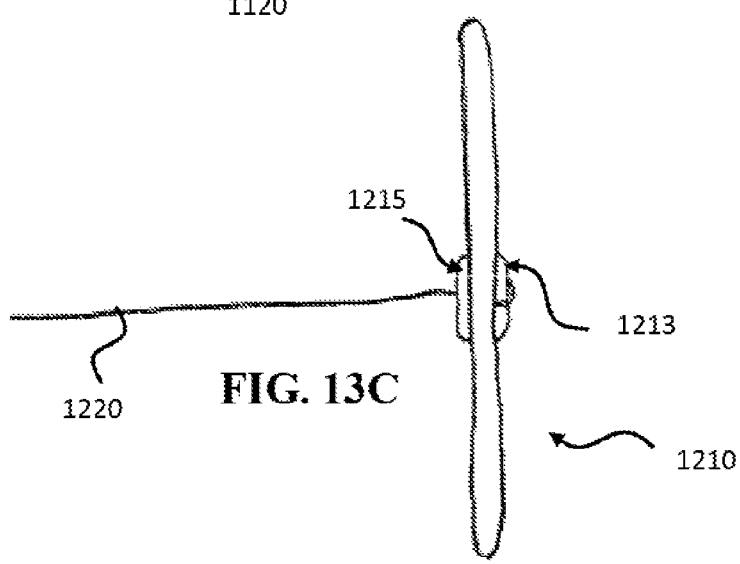
FIG. 13C. A side view of the example embodiment of the button of FIG. 12A in a dilated anchor profile

FIGS. 13A-13C illustrate example embodiments of button as they may look after being deformed to anchor the button in the tissue. FIG. 13A is a perspective view of the example embodiment of the button 1010 of FIG. 10A in a dilated anchor profile showing the suture 1020, the first body portion 1012, the second body portion 1011, the foot connector 1015 and the force connector 1013. FIG. 13B is a perspective view of the example embodiment of the button 1110 of FIG. 11A in a folded anchor profile showing the suture 1120, first body portion 1112, the second body portion 1111 and the foot connector 1115 (the force connector 1113 is not shown). FIG. 13C is a side view of the example embodiment of the button 1210 of FIG. 12A in a dilated anchor profile showing the suture 1220, the foot connector 1215 and the force connector 1213 (the first body portion 1212 and the second body portion 1211 not shown).

The embodiments of anchoring sutures described above are also suitable for anchoring sutures to other body parts such as bones. One embodiment particularly suitable as a bone suture anchoring system is shown in FIGS. 5A and 5B and described below.

Figure 5A:
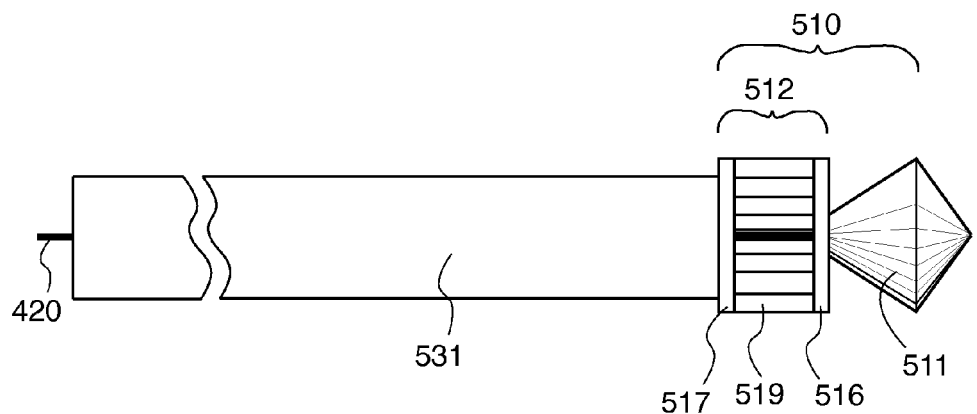
FIG. 5A-5B. A side view of one embodiment of the button in an insertion and a deployed position.
Figure 5B:
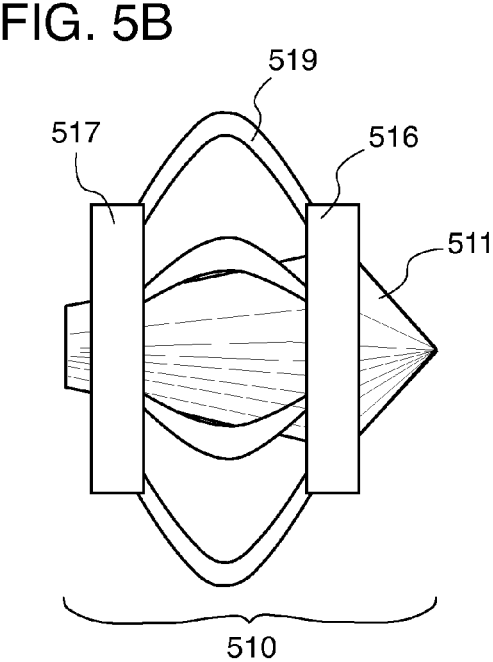

Suture Anchor Assembly in Bone:

Referring to FIGS. 5A and 5B, another embodiment of the suture anchor assembly comprises an expandable first body portion 512 comprising one or more collars with expansion fingers 519, a second retrograde force portion 511 shaped as a trochar, a delivery rod 520 and an impactor 531. Although not limited to, this embodiment is particularly helpful for anchoring sutures to bone.

In this embodiment, the retrograde force body portion 511 is shaped as a wedge pin or trochar with sharpened distal end and a connectable proximal end including a force connector. In this embodiment, the force connector comprises a threaded portion to removably connect with the threaded end of the delivery rod 520. This retrograde force body portion 511 is preferably made from a rigid material such as a metal, plastic or a composite that allows a force to be applied to the threaded end while the sharpened end penetrates bone.

The delivery rod 520 is a rigid or semi-rigid element capable of receiving a force from one end of the rod and transferring that force to retrograde force body portion 511 of the button 510. The rod 520 is cable of receiving and transferring both a forward and retrograde force to the retrograde force body portion 511. The distal end of the rod is configured to mate with the force connector of the retrograde force portion of the button. In this embodiment, the delivery rod distal end is threaded to mate with the force connector. It is contemplated that either of these elements may have the male or female elements of a threaded connection.

Although this embodiment has a delivery rod 520 that connects with retrograde force portion 511 of the button 510 with the use of threaded connections, it is also understood that other means of connecting the delivery rod 520 and the button 510 are possible such as but not limited to mating clips, buttons, protrusions or other connection means.

In this embodiment shown in FIG. 5A, the expandable body portion 512 comprises a proximal collar 517, a distal collar 516 each attached to one or more expanding fingers 519. The collars and fingers are configured so that when forces are applied to urge both collars together, the fingers 519 are forced to flexibly expand outward from the center of the body portion. FIG. 5B illustrates this embodiment in an expanded configuration. This expansion creates the larger profile of the button 510. Although the fingers 519 are able to flexibly expand, they are rigid enough to provide a frictional connection when expanded against bone or other tissue. The expandable body portion 512 of this embodiment can be made of materials that include, but are not limited to metals, metal alloys or non-metallic materials such as nylon, polyethylene, polypropylene or any combination thereof.

Figure 5C:
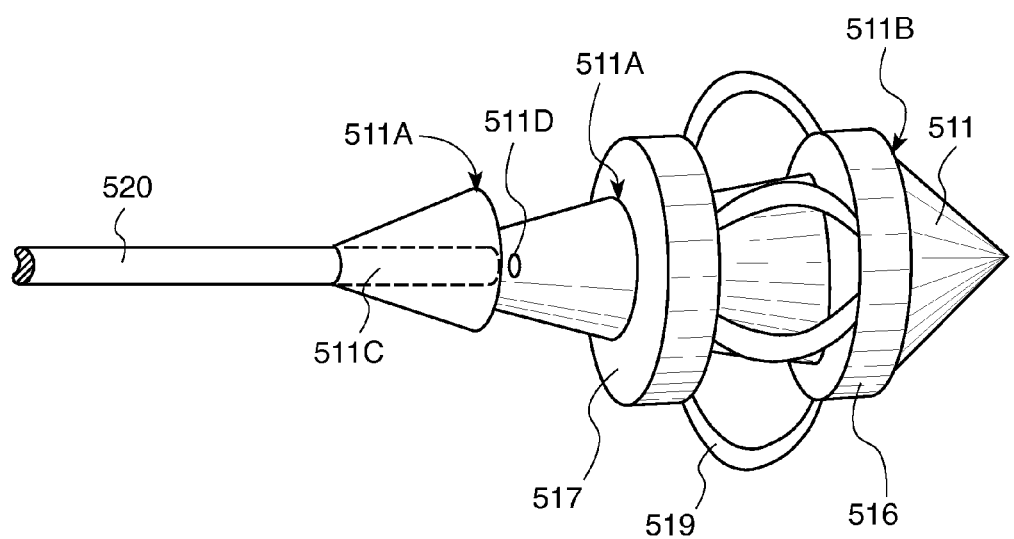
FIG. 5C. A side perspective view of one embodiment of the suture anchor assembly with the button in a deployed position.

In one embodiment, it is also contemplated that the shape of the retrograde force portion includes a hook, protrusion or other means to engage the proximal collar 517 so that the two collars can be retained together and the fingers 519 can be kept in their expanded position after deployment. For one embodiment shown in FIG. 5C, the engagement means comprises one or more protrusions 511A on the retrograde force body portion 511 that compress when forced through one direction of the bore of the proximal collar 517 and expand to prevent the collar from moving in the other direction to retain the collar in one position relative to the protrusions 511A. In this embodiment, the wedge shape of the distal end of the retrograde force body portion 511 creates a wedge edge 511B that transfers the retrograde force against the distal collar 516. The cooperation of the protrusions 511A engagement on the proximal collar 517 and the wedge edge 511B against the distal collar 516 retains the button 510 in a position where the fingers 519 are maintained in an expanded state after deployment. As shown in FIG. 5C, if there are multiple protrusions 511A, the retrograde force body portion 511 will urge the collars together until the fingers expand fully into the defect or bore and the protrusions will be retracted through the proximal collar to engage the proximal collar 517 in a tight position. As also shown in FIG. 5C, a threaded recess 511C provides one means to connect the delivery rod 520 with the retrograde force body portion 511. Also shown is FIG. 5C is an additional suture tie 511D to receive and secure a suture to the anchor assembly.

The impactor 531 is a rigid or semi-rigid element capable of receiving a force from one end of the impactor and transferring that force to the expandable body portion 512. In the embodiment shown, the impactor 531 is a rigid cannula with a longitudinal hollow bore to receive the delivery rod 520. In this embodiment, the bore is shaped to allow the delivery rod 520 to move within the bore while it is also shaped to provide a resisting force on the proximal collar 517 of the button 510. The impactor 531 is shaped to allow the required force to be applied. It is understood that this may require surfaces to either allow the force to be applied frictionally or for the surfaces to be shaped to allow a striking force to be applied. For example, and not for limitation, the impactor 531 may be shaped to have texture about its outer surface to allow the user to frictionally apply the forward force or it can include a flattened surface that would allow the impactor 531 to be struck by a device such as a hammer.

In this embodiment, the cooperation of the elements allows the anchor to be deployed without the need for a traction suture and needle.

It is understood and contemplated that the anchor elements, including the button elements, retrograde force elements and sutures, can be made with both resorbable and non-resorbable materials and each one has its individual characteristics which allow it to work best in tissue or in bone such as cortical and cancellous bone.

Embodiments of the buttons may include rigid buttons made of rigid bioabsorbable or resorbable materials. For illustration only, and not for limitation, the buttons may be made from polymers such as polyglycolic acid, polylactic acid enantiomers, poly-D-L-lactic acid copolymer polyglycolic acid, or a combination of polylactic acid and hydroxyapatite. In the later example embodiment, the polylactic acid dissolves in the body, and the hydroyxapatite may interact with the surrounding tissue to promote bone growth that can help fill in the holes made for or by the buttons.

Embodiments of the buttons may also include rigid buttons made of bioabsorbable or resorbable material such as collagen. In some embodiments, the button swells upon hydration and permits normal bone generation to assist in anchoring the button.

Embodiment of the buttons may also include rigid buttons have elements being made of a combination of bioabsorbable material and non-absorbable material. In some of these embodiments, some elements may have surfaces that are bioabsorbable, such as an exterior surface of the expansion fingers made of collagen, to help assist in anchoring the button into bone.

Meniscal Repair Method with Meniscal Suture Anchor Assembly:

One method of operating one embodiment of the suture anchor assembly shown in FIG. 1 is shown as process steps in FIG. 6. Although particular embodiments of the suture anchor assembly are described, and particular uses of the methods are described, these uses and embodiments are used for illustration purposes and not for limitation. This method 600 comprises the steps of:

Following the starting step 610, a suture anchor assembly is provided as step 620. In one embodiment, the suture anchor assembly comprises a needle, a traction suture, a button, a retrograde force connector and a cannula. The needle is connected to the button with the traction suture and the retrograde force connector is also connected to the button.

Step 630 includes making a small incision to provide access to the tissue to be repaired. For meniscal repair embodiments, this includes making a small incisions on either the medial or lateral joint line down to the outer lining of the joint capsule.

Step 640 includes inserting the needle and traction suture of the suture anchor assembly through the cannula and joint lining and through the defect in the meniscus. The needle is passed from the inside of the joint to the outside while carefully protecting the neurovascular structures.

Figure 7A:
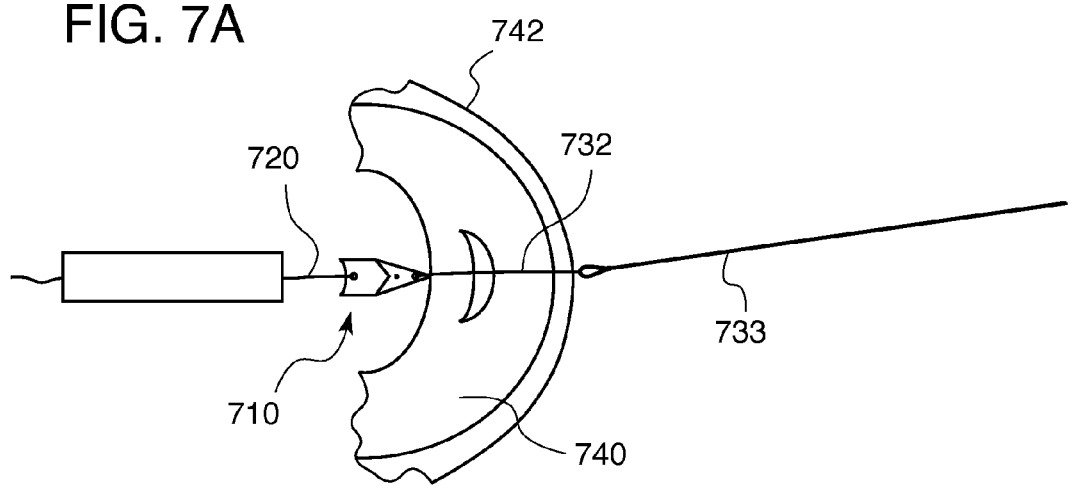
FIG. 7A-7B. A top view of one embodiment of the suture anchor assembly being inserted and deployed in a meniscal repair.

FIG. 7A illustrates the use of one suture anchor assembly in step 640 where the needle 733 is passed through a tissue 740, such as a meniscus, through the defect 741 and outside of the joint lining surface 742. FIG. 7A shows the other elements of the suture anchor assembly prior to pulling the button 710 and retrograde suture 720 (retrograde force element) into the meniscus 740 with the traction suture 732.

Step 650 includes pulling the button through the tissue with the needle and the traction suture. The button need not be pulled entirely through the tissue but may be pulled across the defect and into a position such that the button will anchor into the tissue on the opposing side of the defect. The buttons are preferably not placed near significant neurovascular structures. The buttons are also placed to make sure it is buried in the tissue so that no sharp edges are exposed to other tissues or bone.

In one embodiment for meniscal repair, it is beneficial, but not necessary, in this method to have the button shaped generally flat or planar so that its profile once inserted can be generally parallel to the surfaces of the knee joints to minimize the possibility of protrusions that would irritate the tissues of the joint. For control purposes, the hollow of the cannula can be shaped to receive the button and control its profile during insertion. For example, the button can be planar shaped and the hollow of the cannula can be slot shaped allowing a rotation of the cannula to rotation the planar position of the button.

In one embodiment, of meniscal repair, the final position of the buttons may also be pulled totally through the meniscus to include but not limited to, positions that rest on the outer surface of the meniscus or positions outside of the joint capsule.

Step 660 includes applying a retrograde force on the retrograde force element to deploy the button and urge the tissue defect into the desired position. Typically, but not necessarily, this desired position is to urge opposing edges of a defect together. The retrograde force on the retrograde suture is transferred to a retrograde force to the button which forces the button to deploy and anchor the expansion suture.

It is not necessary to perform step 660 prior to adding a second button and retrograde force element.

Although not required, step 670 includes repeating the above steps (610-660) for at least a second time. For embodiments where the retrograde force element is a retrograde suture, the placement of the needle and the retrograde suture into the tissue is such that it can form sutures such as, but not limited to vertical or horizontal mattress sutures to repair the meniscal defect.

Step 680 includes anchoring the retrograde force element to maintain the tissue defect in the desired position. For embodiments where the retrograde force element is a retrograde suture, the fixation arms of the sutures can be anchored by tying knots in or otherwise knotting the sutures separately or knotting the expansion sutures together to repair the defect.

Step 690 includes removing the traction suture. The traction suture and needle may be removed from the button at any time after the button is positioned properly. One method of removal is to have the traction suture configured as a loop through both the button and the needle whereby cutting one segment of the loop allows the entire suture to be pulled out of the button.

The method is finished with step 695.

In suture anchor assembly embodiments, such as those illustrated in FIGS. 10E and 11D that utilize a forward force to help anchor the button, the second suture is configured and inserted through the tissue similar to the traction suture. After the second suture is used to provide the forward force and the anchor is properly positioned, the suture is removed by cutting a section of the suture loop and pulling the suture through the foot connector and out of the tissue.

Figure 7B:
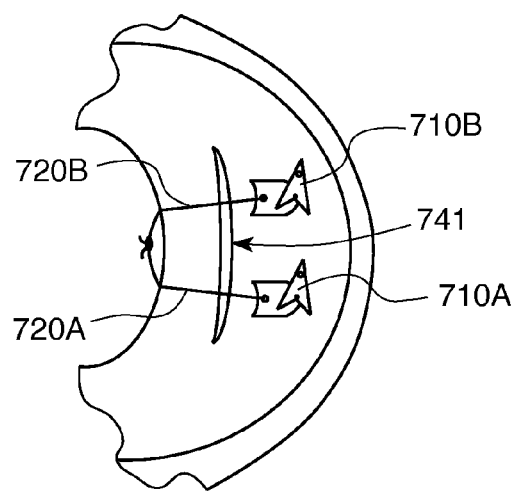

The result of this embodiment for a miniscal repair, as illustrated in 7B, are retrograde sutures 720 that are anchored on either side of a miniscal defect 741 to maintain the tissue 740 in a position to repair or promote healing of the defect. FIG. 7B shows two sutures 720A and 720B anchored by two buttons 710A and 710B across the tissue defect 741.

With this embodiment of the method, incisions that are normally needed in the inside-out procedures to secure the fixation arms of the sutures are not needed. Additionally, the ability to use needles to position the buttons and sutures allows more accurate position of the devices within the tissue and around neuro-vascular structures.

Other methods of use are contemplated as would be envisioned by those skilled in the art. For example, it is contemplated to have pre-tied knots in the sutures to either create a knot in a single suture or to tie two or more sutures together.

It is also contemplated that the method of using needles and traction sutures to position the anchor can be used with other suture anchor systems. Needles and elements to provide the function of the traction suture can be used with existing suture anchor systems.

It is also contemplated that the above method may be performed without the need to use a needle and traction suture to position the button. For these embodiments, it is envisioned that the button may be manufactured to include a distal end that can insert itself and the retrograde suture sufficiently or it can be designed to receive an element such as a guide pin that can be removed once the button is positioned properly. In these embodiments, it is also envisioned that the cannula or other guide means can be designed to provide the force to position the button for meniscal repair.

Although the above description is illustrative of the methods for use with meniscal repair, it is also contemplated that the methods can be applied to the repair of other tissues such as but not limited to stomachs and cartilage associated with joints such as a hip, elbow or shoulder.

Bone Anchoring Method with Bone Suture Anchor Assembly:

One method 800 of using one embodiment of the bone suture anchor assembly shown in FIG. 5 is outlined in FIG. 8 and described below.

Figure 9A:
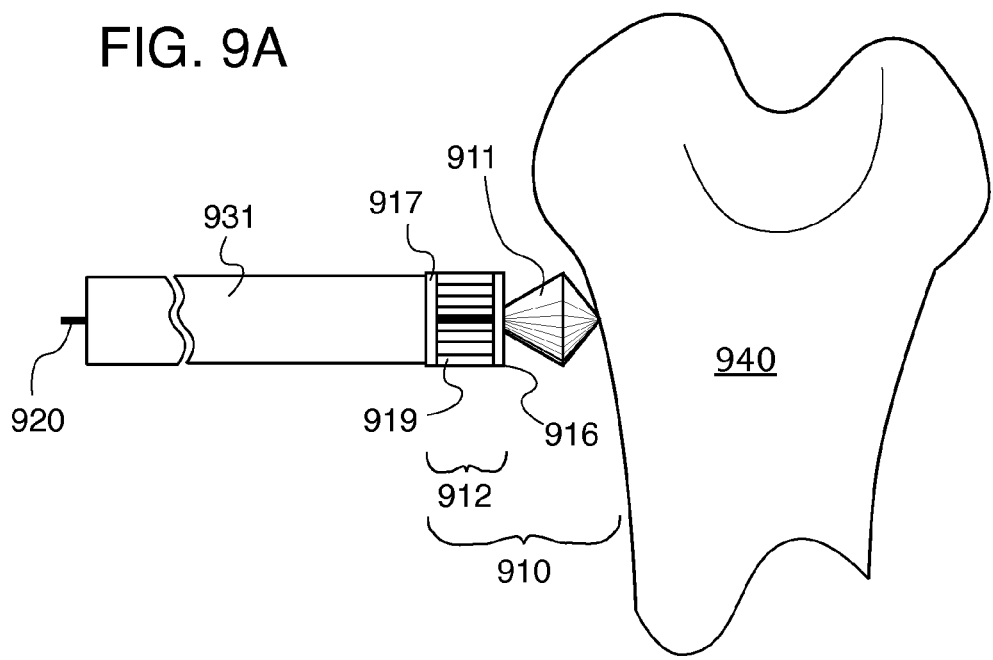
FIG. 9A-9B. A top perspective view of one embodiment of the suture anchor assembly being inserted and deployed to secure a suture in bone.

Following step 810, a bone suture anchor assembly is provided in step 820. In one embodiment, the assembly includes an expandable first body portion comprising one or more collars with expanding fingers, a second retrograde force portion shaped as a trochar, a delivery rod and an impactor. As shown in FIG. 9A, the delivery rod 920 is connected to the proximal end of the retrograde force portion 9110. The delivery rod 920 is received through the proximal collar 917 and distal collar 916 of the expandable first body portion 912 and the impactor 931 is placed around the delivery rod 920 forcing the expandable body potion 912 to be positioned between trochar 9110 and the impactor 931.

Step 830 includes making an incision to provide access to the bone.

Step 840 includes positioning the sharpened end of the trochar against the bone and impacting the anchor assembly into the bone. This step typically includes striking the delivery rod with a weighted object such as a hammer. This forward force is transferred through the delivery rod to the sharp end of the trochar causing the trochar to penetrate the bone. In this step, the sharp trochar is inserted into the bone followed by the insertion of the expandable body portion. The size and shape of the trocar is such that its penetration of the bone forms a cavity of a size to allow the first body portion to also penetrate the bone. Embodiments of this assembly can be inserted into the bone with or without pre-drilling.

Once the trochar and expandable first body portion have penetrated the bone, step 850 includes applying a retrograde force the retrograde force element. In one embodiment, this retrograde force is applied by the delivery rod that is connected to the trochar by the cooperation of the threaded end of the delivery rod and the threaded end of the trochar. The application of this retrograde force subjects the trochar and the distal end of the expandable body portion to that retrograde force while the proximal end of the expandable body portion is subjected to an opposite, forward force from the impactor. These opposing forces force the trochar to pass through the middle of the anchoring device until the outer dimension of the trochar can no longer fit the interior dimension of the distal collar of the first body portion. When the trochar can no longer pass, the retrograde force is transferred to the distal collar forcing the collar to move toward the proximal collar and expand the first body portion until the body portion can no longer expand. This anchor will expand until its profile generally fills the bore created by the trochar. At that point the expanding trochar will stop its retrograde progression. In this position, the anchor is frictionally engaged and held in the bone bore.

Although step 850 includes pulling the trochar retrograde into the expandable body portion, it is also contemplated that the anchor assembly can engage the tissue by maintaining the position of the trochar and forcing the expandable body portion onto the shape of the trochar. This forcing can be applied by the impactor and can also cause the expandable body portion to expand into the bore.

Figure 9B:
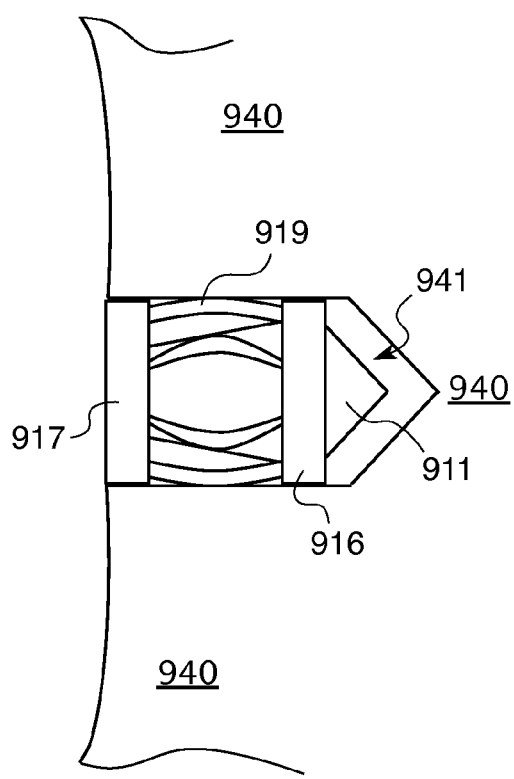

FIG. 9B illustrates this embodiment of the bone suture anchor assembly having been impacted into the bone.

Step 860 includes removing the delivery rod from the trochar.

Step 870 includes attaching a suture or other surgical device to the anchor assembly's first or second body portion. The suture is attached to the anchor assembly under tension which keeps the expandable body portion in an expanded position.

The method is finished with step 880.

The result of this embodiment is shown in FIG. 9B. The trochar 911 (retrograde body portion) is retracted against the distal collar 916. The proximal collar 917 has been retained to urge the fingers 919 to expand. Once expanded, the fingers 919 are frictionally engaged within an opening 941 in the bone originally caused by the trochar 911 being impacted into the bone.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A suture anchor assembly comprising:
   a pliable button configured to engage a tissue;
   the pliable button having a first body portion and a second body portion;
   the first body portion having a force connector;
   a traction suture connected to the first body portion;
   a second suture; separate from the traction suture, connected to the force connector; and
   a means to connect the first body portion and the second body portion whereby a retrograde force on the force connector causes the pliable button to deform and engage the tissue and secure the pliable button in the tissue.

2. The suture anchor assembly of claim 1 whereby:
   the traction suture is configured to position the pliable button in the tissue; and
   a retrograde force on the second suture transfers a retrograde force on the force connector.

3. The suture anchor assembly of claim 1 further comprising:
   a needle;
   the traction suture connecting the needle to the first body portion; and
   whereby a retrograde force on the second suture transfers a retrograde force on the force connector.

4. The suture anchor assembly of claim 1 wherein the second body portion further comprises a foot connector whereby a forward force on the foot connector causes the pliable button to deform and engage the tissue and secure the suture anchor assembly in the tissue.

5. The suture anchor assembly of claim 4 wherein the second suture is configured to transfer a forward force applied to the second suture from a position distal to the suture anchor assembly to the foot connector and cause the pliable button to deform and engage the tissue and secure the suture anchor assembly in the tissue.

6. The suture anchor assembly of claim 4 further comprising:
   a third suture, separate from the traction suture and the second suture, connected to the foot connector and the third suture configured to transfer a forward force applied to the third suture from a position distal to the suture anchor assembly to the foot connector and cause the pliable button to deform and engage the tissue and secure the suture anchor assembly in the tissue.

7. The suture anchor assembly of claim 1 wherein:
   the pliable button comprises a pliable tubular member;
   the means to connect the first body portion and the second body portion comprises a middle body portion of the pliable tubular member; and
   the retrograde force on the force connector causes the pliable tubular member to deform from an insertion profile to a dilated anchor profile.

8. The suture anchor assembly of claim 7 further comprising:
   a needle;
   the traction suture connecting the needle to the pliable tubular member;
   a retrograde force element extending through a longitudinal inner bore of the pliable tubular member; and
   the retrograde force element connected to the force connector whereby a retrograde force on the retrograde force element transfers the retrograde force to the force connector.

9. The suture anchor assembly of claim 7 further comprising:
   a needle;
   the traction suture connecting the needle to the pliable tubular member;
   a foot connector proximal to the second body portion of the pliable tubular member;
   the foot connector shaped to resist eversion of the button when the retrograde force on the force connector causes the tubular member to deform;
   a retrograde force element extending through the foot connector; and
   the retrograde force element is connected to the force connector whereby a retrograde force on the retrograde force element transfers the retrograde force to the force connector.

10. The suture anchor assembly of claim 7 wherein the pliable tubular member further comprises one or more protrusions on an exterior surface of the tubular member whereby the protrusions engage the tissue and secure the anchor assembly to the tissue.

11. The suture anchor assembly of claim 1 wherein:
    the pliable button comprises a pliable sheet;
    the means to connect the first body portion and the second body portion comprises a middle body portion of the pliable sheet; and
    the retrograde force on the force connector causes the pliable sheet to deform from an insertion profile to a folded anchor profile.

12. The suture anchor assembly of claim 11 further comprising:
    a needle;
    the traction suture connecting the needle to the pliable sheet whereby the needle is configured to position the pliable sheet in the tissue;
    a retrograde force element extending alongside a portion of the pliable sheet; and
    the retrograde force element connected to the force connector whereby a retrograde force on the retrograde force element transfers the retrograde force to the force connector.

13. The suture anchor assembly of claim 11 wherein:
    the pliable sheet having a first side, a second side, a length, and at least one foot connector extending through the first side to the second side; and
    a retrograde force element is interwoven through the at least one foot connector and interwoven alongside the first and second side of the pliable sheet whereby the retrograde force on the force connector folds the pliable sheet about the at least one foot connector into the folded anchor profile.

14. The suture anchor assembly of claim 11 further comprising:
a needle;
the traction suture connecting the needle to the pliable sheet;
a foot connector proximal to the second body portion of the pliable sheet;
the foot connector shaped to resist eversion of the pliable sheet when the retrograde force on the force connector causes the pliable sheet to deform;
a retrograde force element extending through the foot connector; and
the retrograde force element connected to the force connector whereby a retrograde force on the retrograde force element transfers the retrograde force to the force connector.

15. The suture anchor assembly of claim 1 wherein:
the pliable button comprises a coiled element;
the means to connect the first body portion and the second body portion comprises a middle body portion of the coiled element; and
the retrograde force on the force connector causes the coiled element to deform from an insertion profile to a dilated anchor profile.

16. The suture anchor assembly of claim 15 further comprising:
a needle;
the traction suture connecting the needle to the coiled element;
a retrograde force element extending within the coiled element; and
the retrograde force element connected to the force connector whereby a retrograde force on the retrograde force element transfers the retrograde force to the force connector.

17. The suture anchor assembly of claim 15 further comprising:
a needle;
the traction suture connecting the needle to the coiled element;
a foot connector proximal to the second body portion of the coiled element;
the foot connector shaped to resist eversion of the pliable button when the retrograde force on the force connector causes the coiled element to deform;
a retrograde force element extending through the foot connector; and
the retrograde force element connected to the force connector whereby a retrograde force on the retrograde force element transfers the retrograde force to the force connector.

18. A suture anchor assembly for anchoring a suture in a tissue comprising:
a pliable button having a first body portion and a second body portion;
a middle body portion connecting the first body portion and the second body portion;
a force connector connected to the first body portion;
a first suture connected to the force connector;
a foot connector connected to the second body portion;
a forward force element connected to the foot connector;
the forward force element comprising a second suture, separate from the first suture; and
the foot connector shaped to resist eversion of the pliable button whereby a forward force on the first suture applied from a position distal to the pliable button causes the middle body portion to deform and engage a tissue and secure the pliable button in the tissue.

19. The suture anchor assembly of claim 18 wherein:
the pliable button is bioabsorbable; and
the anchor assembly further comprises a retrograde force element connected to the force connector whereby a retrograde force on the retrograde force element is transferred to the force connector.

20. A suture anchor assembly comprising:
a pliable button configured to engage a tissue;
the pliable button having a first body portion and a second body portion;
the first body portion having a force connector;
a means to connect the first body portion and the second body portion whereby a retrograde force on the force connector causes the pliable button to deform and engage the tissue and secure the pliable button in the tissue;
the pliable button comprises a pliable sheet;
the means to connect the first body portion and the second body portion comprises a middle body portion of the pliable sheet;
the retrograde force on the force connector causes the pliable sheet to deform from an insertion profile to a folded anchor profile;
a needle;
a traction suture connecting the needle to the pliable sheet;
a foot connector proximal to the second body portion of the pliable sheet;
the foot connector shaped to resist eversion of the pliable sheet when the retrograde force on the force connector causes the pliable sheet to deform;
a retrograde force element extending through the foot connector;
the retrograde force element comprising a second suture, separate from the traction suture; and
the retrograde force element connected to the force connector whereby a retrograde force on the retrograde force element transfers the retrograde force to the force connector.

* * * * *